United States Patent
Kinoshita

(10) Patent No.: US 8,104,363 B2
(45) Date of Patent: Jan. 31, 2012

(54) SEALING STATUS INSPECTING APPARATUS AND SEALING STATUS INSPECTING METHOD

(75) Inventor: Shigehiro Kinoshita, Tokyo (JP)

(73) Assignee: Tetra Laval Holdings & Finance S.A., Pully (CH)

( * ) Notice: Subject to any disclaimer, the term of this patent is extended or adjusted under 35 U.S.C. 154(b) by 693 days.

(21) Appl. No.: 12/097,210

(22) PCT Filed: Dec. 14, 2006

(86) PCT No.: PCT/JP2006/324933
§ 371 (c)(1),
(2), (4) Date: Jan. 5, 2009

(87) PCT Pub. No.: WO2007/072729
PCT Pub. Date: Jun. 28, 2007

(65) Prior Publication Data
US 2009/0165536 A1 Jul. 2, 2009

(30) Foreign Application Priority Data
Dec. 20, 2005 (JP) .................... 2005-366010

(51) Int. Cl.
*G01N 27/61* (2006.01)
(52) U.S. Cl. ............ 73/865.8; 73/49.3; 73/52; 73/866.5
(58) Field of Classification Search ............ 73/40–49.8, 73/52, 865.8, 866.5
See application file for complete search history.

(56) References Cited

U.S. PATENT DOCUMENTS

| | | | | |
|---|---|---|---|---|
| 3,254,526 A | * | 6/1966 | Yarbrough | 73/40 |
| 3,811,317 A | * | 5/1974 | Leonard et al. | 73/40 |
| 3,937,064 A | * | 2/1976 | Wolf et al. | 73/40 |
| 4,728,800 A | * | 3/1988 | Surka | 250/559.42 |

(Continued)

FOREIGN PATENT DOCUMENTS

| | | |
|---|---|---|
| EP | 1 057 619 A1 | 12/2000 |
| EP | 1 347 291 A1 | 9/2003 |
| JP | 6-171620 A | 6/1994 |

(Continued)

OTHER PUBLICATIONS

International Search Report for PCT/JP2006/324933 and mailed on Mar. 13, 2007.

*Primary Examiner* — David A. Rogers
(74) *Attorney, Agent, or Firm* — Buchanan Ingersoll & Rooney PC

(57) ABSTRACT

A laminated packaging material is composed of a thermoplastic material outermost layer, a paper base material layer, a conductive barrier layer and a heat sealing innermost layer. An apparatus inspects an opening section, which is formed by at least partly eliminating the thermoplastic material outermost layer and the paper base material layer and by being sealed to be easily opened. In the apparatus, a probe electrode and a grounding electrode are arranged on the outer side and the inner side of the opening section, a current flowing between the probe electrode and the grounding electrode is detected by using the conductive barrier layer, and the sealing status of the opening section is inspected by a judging mechanism.

8 Claims, 6 Drawing Sheets

U.S. PATENT DOCUMENTS

| | | | | |
|---|---|---|---|---|
| 4,768,371 A * | 9/1988 | Joshi | ................................ | 73/40.7 |
| 6,920,793 B2 * | 7/2005 | Stauffer | ............................ | 73/630 |
| 7,030,400 B2 * | 4/2006 | Rivera et al. | .............. | 250/559.11 |
| 7,167,803 B2 | 1/2007 | Kinoshita et al. | | |
| 7,498,817 B2 * | 3/2009 | Redko et al. | .................... | 324/464 |
| 7,623,699 B2 * | 11/2009 | Floeder et al. | ................. | 382/149 |
| 7,649,365 B1 * | 1/2010 | Zapalac et al. | ............ | 324/754.23 |
| 2002/0152814 A1 * | 10/2002 | Binder et al. | ..................... | 73/588 |
| 2003/0110832 A1 * | 6/2003 | Carey et al. | ......................... | 73/40 |
| 2005/0008765 A1 * | 1/2005 | Karjanmaa | ......................... | 427/8 |
| 2005/0232475 A1 * | 10/2005 | Floeder et al. | ................. | 382/141 |

FOREIGN PATENT DOCUMENTS

| | | | | |
|---|---|---|---|---|
| JP | 2000-249618 A | | | 9/2000 |
| JP | 2004-101412 A | | | 4/2004 |
| JP | 2004-132713 A | | | 4/2004 |
| JP | 2004132714 A | * | | 4/2004 |
| JP | 2004-144503 A | | | 5/2004 |
| JP | 2005-121054 A | | | 5/2005 |
| JP | 2005-326276 | | | 11/2005 |
| JP | 2005326276 A | * | | 11/2005 |
| JP | 2008150084 A | * | | 7/2008 |

* cited by examiner

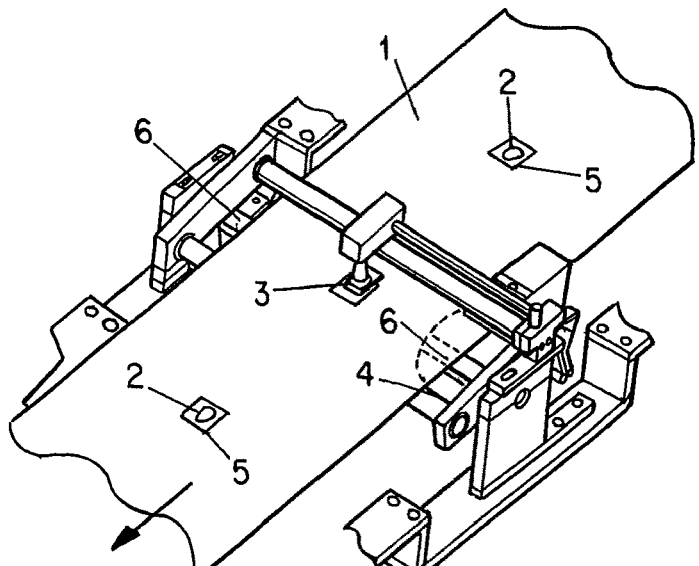
Fig. 1
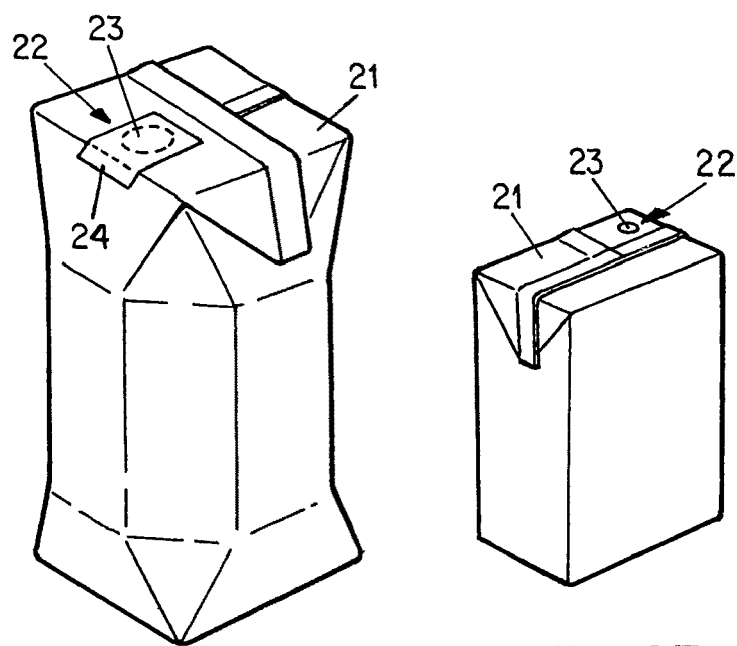
Fig. 2A
PRIOR ART
Fig. 2B
PRIOR ART

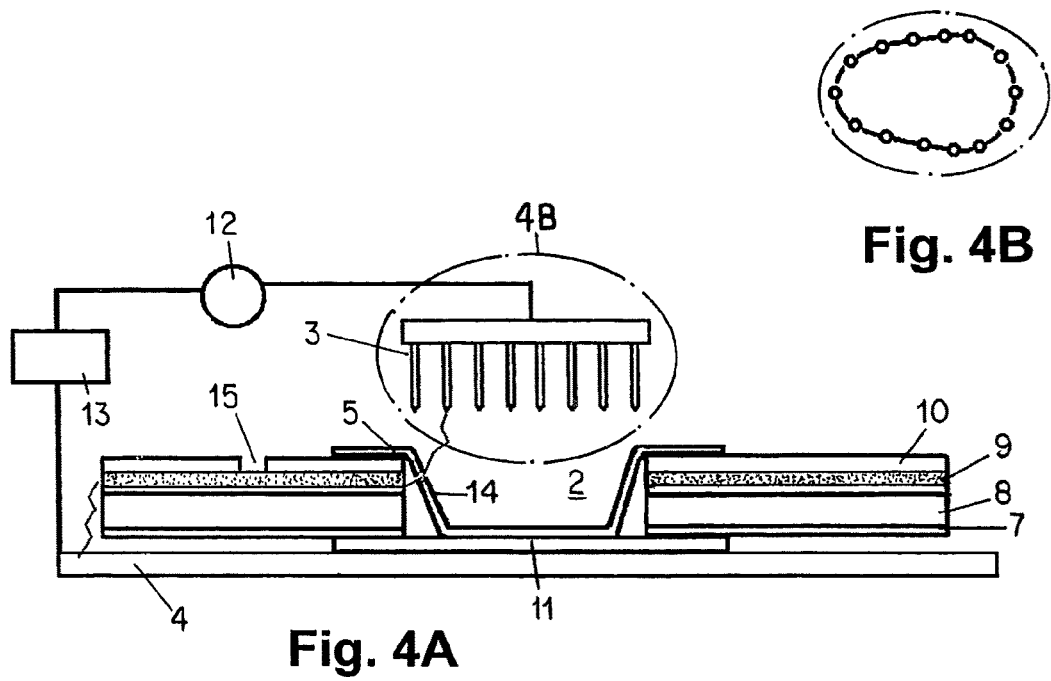
Fig. 4B
Fig. 4A
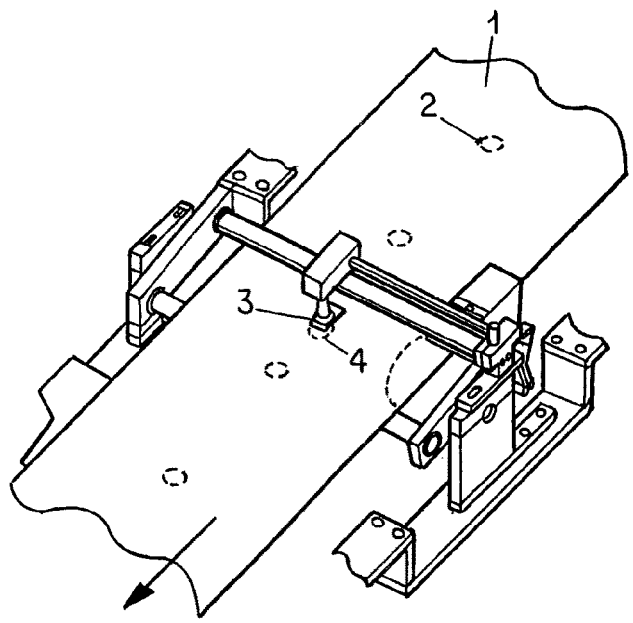
Fig. 5

[Fig. 7]

SEALING STATUS INSPECTING APPARATUS AND SEALING STATUS INSPECTING METHOD

TECHNICAL FIELD

The present invention relates to an apparatus for and a method of inspecting a sealed condition of a paper-made packaging container with a liquid food product such as juice or milk contained filled therein as well as of a laminated material for packaging.

BACKGROUND TECHNOLOGY

A paper-made packaging container capable of preserving drinks or fluidized foods such as milk, juice, and mineral water at the room temperature is obtained, for instance, from an outermost layer made of a thermoplastic material, a paper-made substrate layer, a conductive barrier layer (made of, for instance, aluminum foil), and a heat-sealable innermost layer.

A packaging container for a liquid food product has an opening for mounting thereon a lip from which the liquid food product is poured out or a cover, and a straw hole (opening) through which a straw is inserted, and the opening and the straw hole are provided at a vertex portion of the container. Furthermore a through hole as an opening is formed in the packaging container, and the opening is sealed with a barrier pull-tab from the outside and also with a patch film from the inside.

FIG. 2 illustrates two examples of a packaging container. An opening 22 from which a liquid food product is poured out is formed at a vertex portion of a container 21 shown in FIG. 2A, and a through hole 23 is formed in the laminated material for packaging, and an area including the through hole 23 is sealed by a paper-made substrate layer with an outermost layer made of a thermoplastic material, a conductive barrier layer, and a heat-sealable innermost layer laminated on both surfaces thereof.

FIG. 3 illustrates an example of an apparatus used for manufacturing a packaging container shown in FIG. 2.

In a filling machine shown in the example, a packaging material web 31 having thermoplastic material layers on both outer and inner layers of the paper-made substrate layer and wound up into a form like a roll is fed out and transferred by a roller in the filling machine; a through hole is provided by an pull-tab applicator 33 in the packaging material; the area is sealed with a barrier pull-tab from the outer side and with a batch fill from the inner side; the packaging material web is sterilized in a sterilizer bath 32; the packaging material is formed into a tube-like form with a forming roller 34; both end sides of the packaging material are overlaid on each other to form an overlap; the overlapped area is sealed with a longitudinal seal element 36 along the longitudinal direction of the tubular section; a liquid food product is filled into the tube from a filling pipe 35; this tube is fed downward by a length corresponding to one packaging container and is sealed in the transversal direction with a transversal sealing apparatus (not shown) to successively form pillow-like preliminarily formed bodies 37; the pillow-like preliminarily formed bodies linked to each other are separated to provide discrete preliminarily formed bodies by cutting a sealed zone between the adjoining preliminarily formed bodies at an intermediate point; and upper and lower flaps of the preliminarily formed body is bent with a finally forming machine 38 to provide a finally formed packaging container 39.

A container produced for preserving a quality of a paper-made packaging container is required to be inspected for such properties as the appearance, the sealing capability, and the capability of maintaining the fragrance. Because there is not the paper-made substrate layer in the opening and an undesirable condition for sealing may occur, it is especially desirable to inspect the sealing capability of the opening. There have been proposed various ideas for improvement of the sealing capability.

The ideas include, for instance, a seal inspection method enabling precise inspection of a sealed condition in a sealed section by energizing an aluminum foil layer inside a packaging material forming a paper-made container to measure an electrostatic capacitance (Refer to patent document 1), and a method in which flaps are peeled off from a wall of the container with the processing unit; a the container wall is cut with a sample preparing unit to prepare a sample; a sealing quality is inspected with a seal quality inspecting unit; a sealed zone is inspected with an image processor; and damages of the sealed zone are inspected with a seal damage inspecting unit (Refer to patent document 2).

With the conventional techniques as described above, however, it is required to break up a paper-made container for inspection, or to prepare a sample for inspection by cutting a container wall with a sample preparing unit. For the reasons described above, it is impossible to inspect all products on a production line.

[Patent document 1] Japanese Patent Laid-Open Publication No. 2005-326276

[Patent document 2] Japanese Patent Laid-Open Publication No. 2004-144503

DISCLOSURE OF THE INVENTION

Problems to be Solved by the Invention

An object of the present invention is to provide a sealed condition inspection apparatus and a sealed condition inspection method not requiring breaking up nor cutting of a paper-made container to prepare a sample for testing, and enabling inspection of all products on a production line.

Means for Solving the Problems

To achieve the objective described above, the present invention provides a sealed condition inspection apparatus that inspects an opening provided on a laminated packaging material having an thermoplastic outermost layer, a paper-made substrate layer, a conductive barrier layer, and a heat-sealable innermost layer, the opening prepared by partially cutting at least the thermoplastic outermost layer and the paper-made substrate layer and also the opening sealed in the easily-openable condition, and in the apparatus, a probe electrode and an earth electrode are provided outside and inside the opening, a current flowing between the probe electrode and the earth electrode is detected with the conductive barrier layer, and a sealed condition of the opening is inspected by a determining unit.

In a sealed condition inspection apparatus according to a first preferable embodiment of the present invention, an opening is formed with a through hole provided on a laminated packaging material and an area including an outer peripheral portion of the through hole is sealed with a barrier pull-tag from the outside and with a patch film from the inside; the probe electrode has a form covering up to the outer peripheral portion of the through hole and is provided on the patch film from the inside; the earth electrode is provided so that detection can be made for the conductive barrier layer on at least one edge face of the web-like laminated packaging material;

and the determining unit detects conductivity between the probe electrode and the conductive barrier layer on the edge face of the through hole via the patch film to determine whether the sealed condition is defective or not.

In a sealed condition inspection apparatus according to a second preferable embodiment of the present invention, an opening is formed with a through hole provided on a paper-made substrate layer, an area including the through hole is sealed by laminating an thermoplastic material outermost layer, a conductive barrier layer, and a heat-sealable innermost layer; the probe electrode has a form covering up to the outer peripheral portion of the through hole and is provided on the patch film from the inside; the earth electrode is provided so that detection can be made for the conductive barrier layer on at least one edge face of the web-like laminated packaging material; and the determining unit determines conductivity via the conductive barrier layer through a space penetrating the thermoplastic material outermost layer, the conductive barrier layer, and the heat-sealable innermost layer within the through hole to determine whether the sealed condition is defective or not.

The present invention provides a sealed condition inspection method for inspecting an opening provided on a laminated packaging material having a thermoplastic outermost layer, a paper-made substrate layer, a conductive barrier layer, and a heat-sealable innermost layer, the opening prepared by partially cutting at least the thermoplastic outermost layer and the paper-made substrate layer and also the opening sealed in the easily-openable condition, wherein a probe electrode and an earth electrode are provided outside and inside the opening;

a high voltage is loaded between the probe electrode and the earth electrode and a current flowing between the probe electrode and the earth electrode is detected with the conductive barrier layer; and a sealed condition of the opening is inspected by a determining unit.

In a sealed condition inspection method according to a first preferable embodiment of the present invention, the opening is formed with a through hole provided on a laminated packaging material and an areas including an outer peripheral portion of the through hole is sealed with a barrier pull-tag from the outside and with a patch film from the inside;

the probe electrode has a form covering up to an outer peripheral portion of the through hole and is provided on the patch film from the inner side;

the earth electrode is provided so that the conductive barrier layer on at least one end face of the we-like laminated packaging material can be detected; and the determining unit detects conduction between the probe electrode and the conductive barrier layer on the end face of the through hole via the patch film to determine whether the sealed condition is defective or not.

In a sealed condition inspection method according to a second embodiment of the present invention, the opening is formed with a through hole provided on the paper-made substrate layer and an area including the through hole is sealed by laminating the thermoplastic material outermost layer, the conductive barrier layer, and the heat-sealable innermost layer;

the probe electrode has a form covering at least an outer peripheral portion of the through hole and is provided on the heat-sealable innermost layer from the inner side;

the earth electrode has a form covering up to an outer peripheral portion of the through hole and is provided on the thermoplastic material outermost layer from the outer side; and the determining unit detects conduction by a void penetrating the thermoplastic material outermost layer, the conductive barrier layer, and the heat-sealable innermost layer inside the through hole to determine whether the sealed condition is defective or not.

In a sealed condition inspection method according to a third embodiment of the present invention, the opening provided at a vertex portion of a container is formed with a through hole provided on the paper-made substrate layer, and an area including the through hole is sealed by laminating the thermoplastic material outermost layer, the conductive barrier layer, and the heat-sealable innermost layer;

the probe electrode has a form covering at least an outer peripheral portion of the through hole and is provided on the thermoplastic outermost layer from the outer side;

the earth electrode is provided so that the conductive barrier layer can be detected provided at least one end face of the laminated packaging material formed on the container; and the determining unit detects conduction via the conduction barrier by a void penetrating the thermoplastic material outermost layer, the conductive barrier layer, and the heat-sealable innermost layer inside the through hole to determine whether the sealed condition is defective or not.

EFFECTS OF THE INVENTION

The present invention provides the following advantages.

The present invention provides an apparatus for inspecting an opening provided on a laminated packaging material having a thermoplastic material outermost layer, a paper-made material layer, a conductor barrier layer, and a heat-sealable innermost layer.

This opening is formed by partially cutting at least the thermoplastic material outermost layer and the paper-made material layer and is sealed in the easily openable condition. Because the paper-made material layer is not present in the opening portion, the opening is mechanically weak and has a step or a peripheral portion, and therefore a sealing defect may occur, which in turn may give negative defects to the content. With the present invention, it is possible to detect a container having a sealing defect in the opening and also to prevent the container from being shipped as a product.

In the sealed condition inspection apparatus according to the present invention, the probe electrode and the earth electrode does not mechanically contact a surface of a laminated packaging material, and are provided in adjacent to each other in the outer side and in the inner side respectively, so that an outer surface of the laminated packaging material are not damaged by the electrodes (during inspection) and all products (packaging material and packaged containers) can be inspected on the production line).

In the sealed condition inspection apparatus according to the present invention, the conductor barrier layer which is one of layers in the laminated packaging material, and therefore parts, means and tools other than the electrodes are not required, which contributes to simplification of the apparatus.

In this specification, the use of the conductor barrier layer for inspection means that an electric current is flown between a probe electrode and an earth electrode by making use of conductivity of a barrier layer or by energizing the barrier layer when there is any defect, or that an electric current is flown between a probe electrode and an earth electrode by energizing through a pin hole, cracking, or a space inside the barrier layer when there is any defect.

In the sealed condition according to a first preferable embodiment of the present invention, an opening is formed with a through hole provided on a laminated packaging material and an area including an outer peripheral portion of the through hole is sealed with a barrier pull-tag from the outside and with a patch film from the inside; the probe electrode has a form covering up to the outer peripheral portion of the through hole and is provided on the patch film from the inside; the earth electrode is provided so that detection can be made for the conductive barrier layer on at least one edge face of the web-like laminated packaging material; and the determining unit detects conductivity between the probe electrode and the conductive barrier layer on the edge face of the through hole via the patch film to determine whether the sealed condition is defective or not.

Each layer of the laminated packaging material is exposed on an end face of a peripheral portion of the through hole, and therefore the barrier effect is not provided in the opening. The opening is sealed with a pull-tab providing the barrier effect from the outer side and also with a patch film from the inner side to cover the peripheral portion. If there is any pin hole in the peripheral portion of the inner patch film which is relatively weak mechanically, a content liquid may ooze out from the portion or atmospheric air may come into the inside, which may negatively affect the content.

Because the probe electrode is provided on the patch film from the inner side, when there is any pin hole in the peripheral portion of the inner patch film, the probe electrode and the conductive barrier layer on an end face of the through holt are conducted to each other via the pin hole, and furthermore inside of the conductive barrier layer becomes conductive. Furthermore, because the earth electrode is provided so that the conductive barrier layer at least on an end face of the web-like laminated packaging material can be detected, when any defect is caused by the pin hole, a current flows between the probe electrode and the earth electrode via the conductive barrier layer.

In addition, the probe electrode has a form covering up to an outer peripheral portion of the through hole, even if there is any pin hole (causing no defect) at a position off from the outer peripheral portion of the through hole inside the inner patch film or inside the heat-sealable innermost layer, an electric current does not flow between the probe electrode and the earth electrode, so that a malfunction detecting a not-defective condition as a defective condition can be prevented.

In a sealed condition inspection apparatus according to a second preferable embodiment of the present invention, an opening is formed with a through hole provided on a paper-made substrate layer, an area including the through hole is sealed by laminating an thermoplastic material outermost layer, a conductive barrier layer, and a heat-sealable innermost layer.

Because of the configuration, the opening can be inspected before a packaging material is formed into a container and a content is filled in the container. This configuration be preferable because inspection of a sealed condition of the opening becomes more difficult after the packaging material is formed into a container and a content is filled in the container.

In the sealed condition inspection apparatus according to the second preferable embodiment of the present invention, a probe electrode having a form covering up to at least a peripheral portion of the through hole is provided on a heat-sealable innermost layer from the inner side.

Even when there is any pin hole (causing no defect) at a position off from the outer peripheral portion of the through hole inside the inner patch film or inside the heat-sealable innermost layer, an electric current does not flow between the probe electrode and the earth electrode, so that a malfunction detecting a not-defective condition as a defective condition can be prevented.

Furthermore, the earth electrode has a form covering up to the peripheral portion of the through hole, a malfunction enabling conductivity with the conductive barrier layer on an end face of the web-like laminated packaging material never occurs.

In this embodiment, the determining unit detects conductivity through a void penetrating the thermoplastic material outermost layer, the conductive barrier layer, and the heat-sealable innermost layer to determine whether the sealed condition is defective or not.

In a sealed condition inspection apparatus according to a third preferable embodiment of the present invention, an opening at a vertex of a container is formed with a through hole provided on a paper-made substrate layer, and an area including the through hole is sealed by laminating a thermoplastic material outermost layer, a conductive barrier layer, and a heat-sealable innermost layer.

In this embodiment, inspection can be made after a packaging material is formed into a container and a content is filled in the container, namely after a final product is manufactured. Because of the configuration, a product with high reliability can be shipped.

Furthermore a probe electrode having a form covering up to at least a peripheral portion of the through hole is provided on the thermoplastic material outermost layer from the outer side.

An earth electrode is provided so that the conductive barrier layer provided at least on an end face of the laminated packaging material formed into a container can be detected.

When the web-like packaging material is formed into a container, the conductive barrier layer at an end face of the laminated packaging material is exposed when bent in various ways. Conductivity with the earth electrode is provided by making use of the exposed face.

When any defect is found during a sealed condition inspection in the third preferable embodiment of the present invention, a void penetrating the thermoplastic material outermost layer, the conductive barrier layer, and the heat-sealable innermost layer is generated. The conductive barrier layer is exposed on an end face of the void or the pin hole, and an electric current flows between the probe electrode and the earth electrode via the conductive face. The determining unit detect the conductivity to determine whether the sealed condition is defective or not.

BRIEF DESCRIPTION OF THE DRAWINGS

FIG. 1 provides a perspective view illustrating a packaging container and an unsealing apparatus for the packaging container according to a first embodiment of the present invention, and a partially enlarged view illustrating a function of a hinge section.

FIG. 2 is a side view illustrating an appearance of an unsealing apparatus for a container according to a second embodiment of the present invention.

FIG. 4 is a view illustrating functions of the first hooking section and the second hooking section of the hinge section in an unsealing apparatus for a container according to a second embodiment of the present invention.

FIG. 5 is a view illustrating functions of the first hooking section and the second hooking section of the hinge section in an unsealing apparatus for a container according to a second embodiment of the present invention.

DESCRIPTION OF SIGNS

1: Packaging material
2: Opening
3: Probe electrode
4: Earth electrode
9: Conductive barrier layer

BEST MODE FOR CARRYING OUT THE INVENTION

Embodiments of the present invention are described in detail below with reference to the related drawings.

Figure 3:
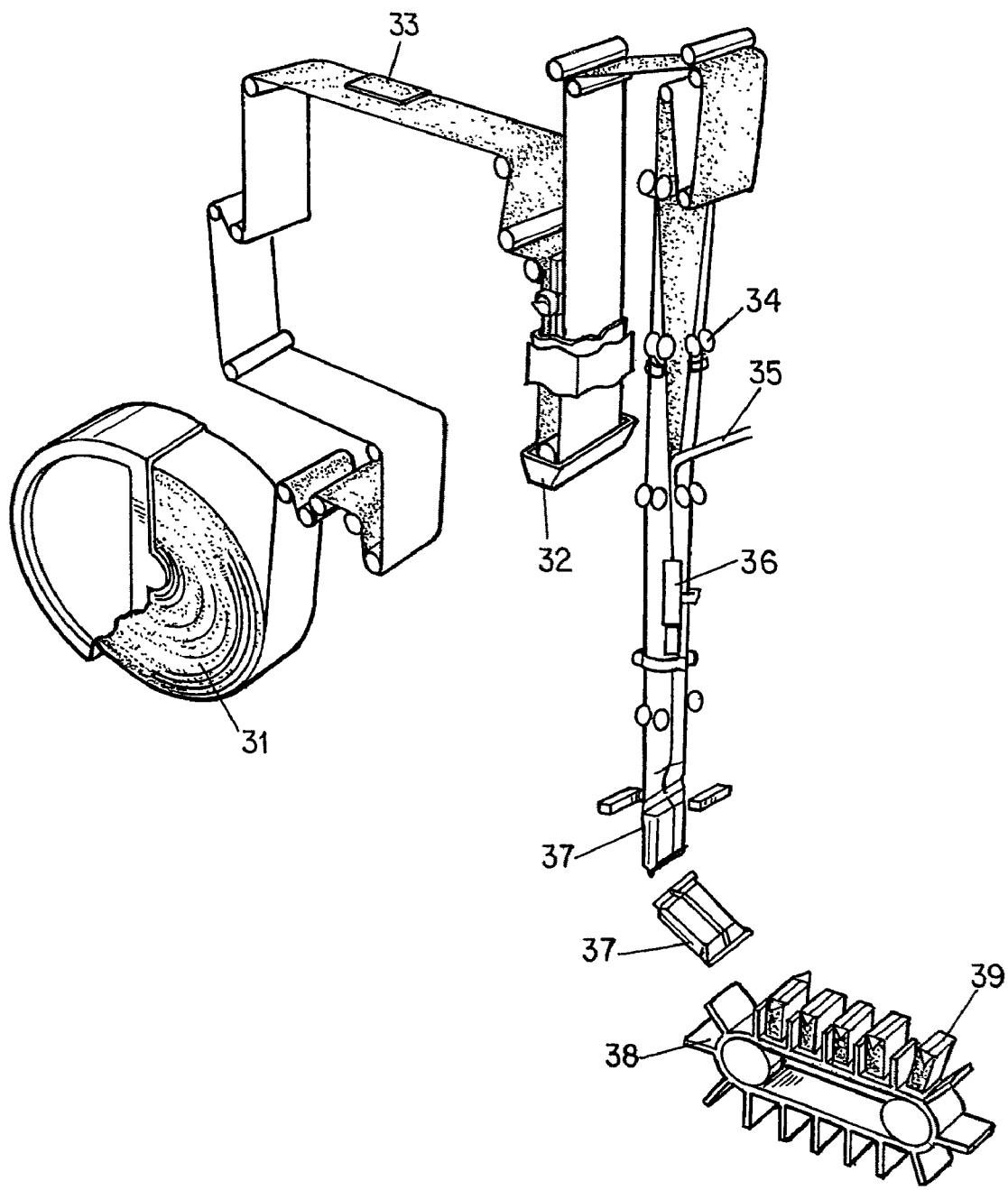
FIG. 3 is a view illustrating functions of a first hooking section and a second hooking section of the hinge section in an unsealing apparatus for a container according to a second embodiment of the present invention.
Figure 6:
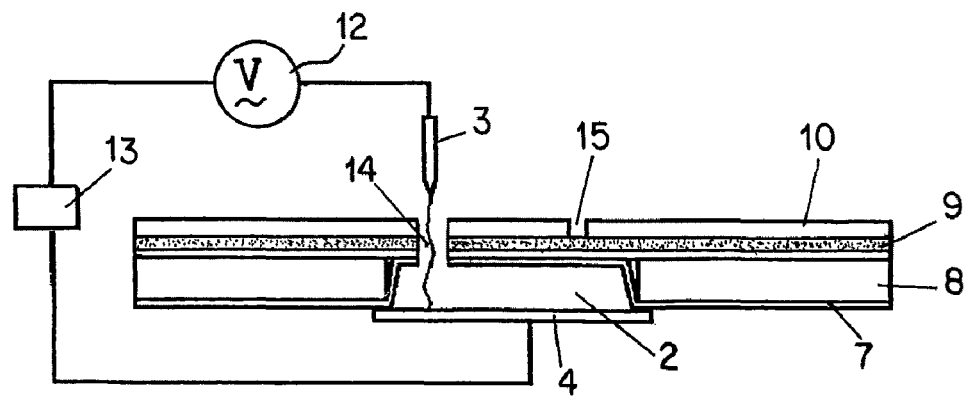
FIG. 6 is a view illustrating functions of the first hooking section and the second hooking section of the hinge section in an unsealing apparatus for a container according to a second embodiment of the present invention.
Figure 7A:
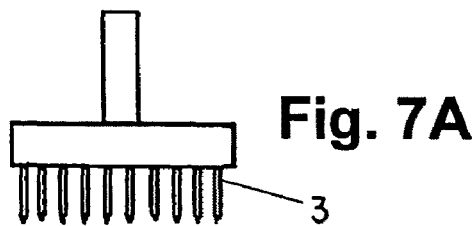
FIG. 7 is a perspective view illustrating an appearance of the unsealing apparatus for a container according to the second embodiment of the present invention.
Figure 7B:
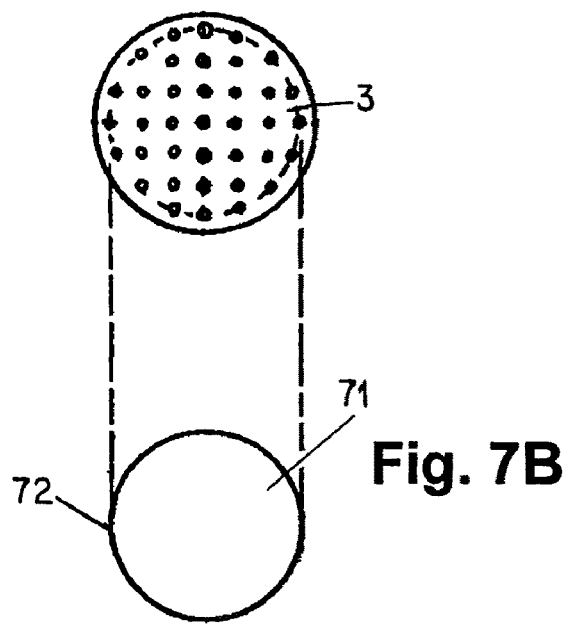
Figure 8:
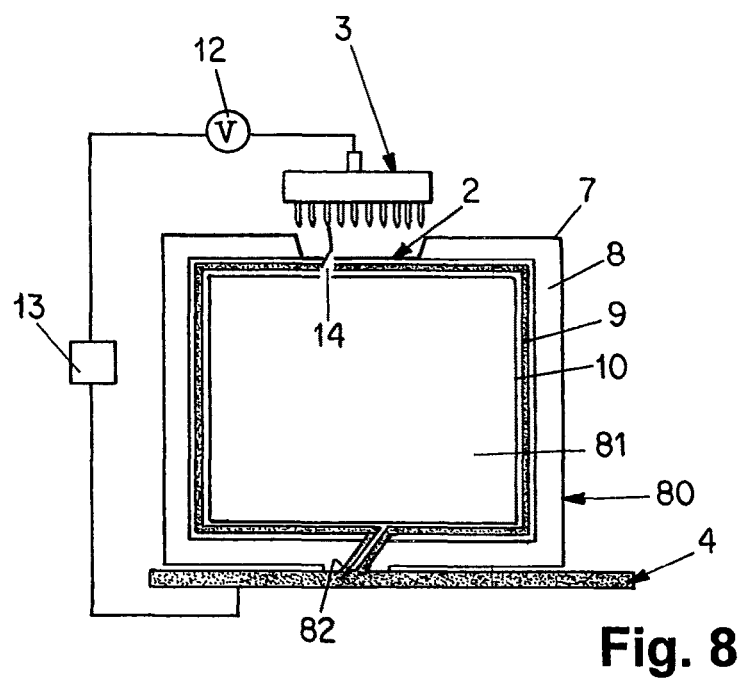
FIG. 8 is a perspective view illustrating an example of the conventional hybrid packaging container.
Figure 9:
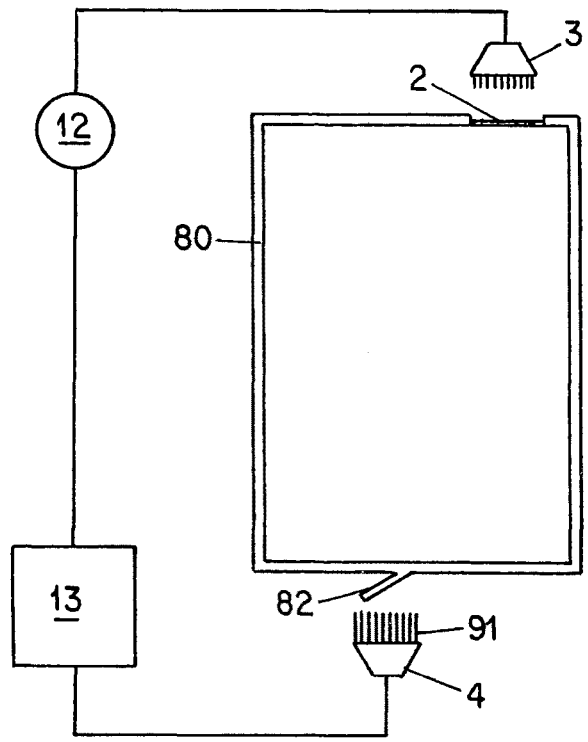
FIG. 9 is a conceptual perspective view illustrating an example of an apparatus used for manufacturing the hybrid packaging container.
Figure 10:
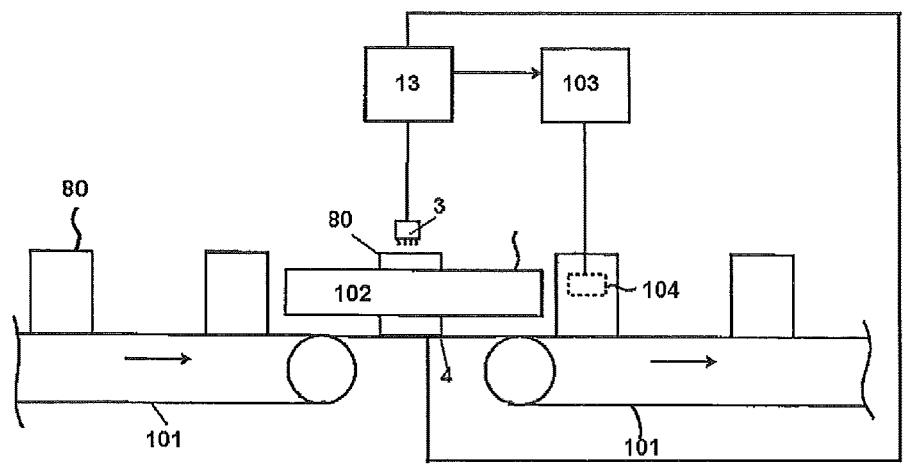
FIG. 10 provides a side view, a front view, a flat view, and a bottom view each illustrating an appearance of a packaging container and an unsealing apparatus for the container according to a second embodiment of the present invention.
Figure 11:
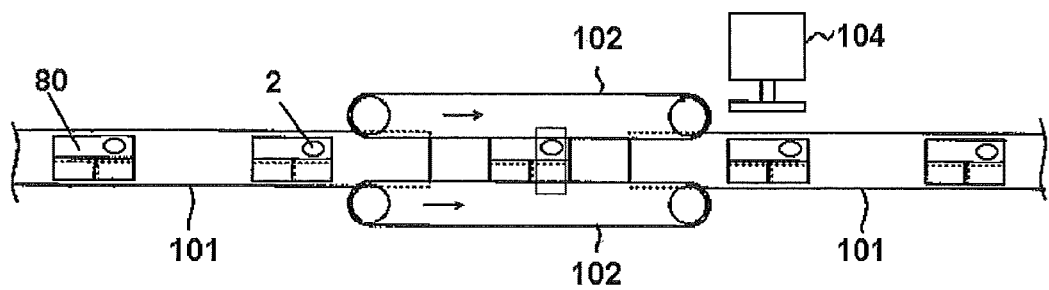
FIG. 11 is a general front view illustrating the model shown in FIG. 10 in which an inspection apparatus according to a third embodiment of the present invention is incorporated in a production line.

FIG. 1 provides a perspective view illustrating a packaging container and an unsealing apparatus for the packaging container according to a first embodiment of the present invention, and a partially enlarged view illustrating a function of a hinge section;

FIG. 2 is a side view illustrating an appearance of an unsealing apparatus for a container according to a second embodiment of the present invention;

FIG. 3 is a view illustrating functions of a first hooking section and a second hooking section of the hinge section in an unsealing apparatus for a container according to a second embodiment of the present invention;

FIG. 4 is a view illustrating functions of the first hooking section and the second hooking section of the hinge section in an unsealing apparatus for a container according to a second embodiment of the present invention;

FIG. 5 is a view illustrating functions of the first hooking section and the second hooking section of the hinge section in an unsealing apparatus for a container according to a second embodiment of the present invention;

FIG. 6 is a view illustrating functions of the first hooking section and the second hooking section of the hinge section in an unsealing apparatus for a container according to a second embodiment of the present invention;

FIG. 7 is a perspective view illustrating an appearance of the unsealing apparatus for a container according to the second embodiment of the present invention;

FIG. 8 is a perspective view illustrating an example of the conventional hybrid packaging container;

FIG. 9 is a conceptual perspective view illustrating an example of an apparatus used for manufacturing the hybrid packaging container;

FIG. 10 provides a side view, a front view, a flat view, and a bottom view each illustrating an appearance of a packaging container and an unsealing apparatus for the container according to a second embodiment of the present invention; and FIG. 11 is a general front view illustrating the model shown in FIG. 10 in which an inspection apparatus according to a third embodiment of the present invention is incorporated in a production line.

The inspection apparatus according to the first embodiment of the present invention of the present invention is used for inspection of an opening 2 of a web-like laminated packaging material having a thermoplastic material outermost layer, a paper-made substrate layer, a conductive barrier layer, and a heat-sealable innermost layer.

The opening 2 is formed by cutting off the thermoplastic material outermost layer, the paper-made substrate layer, the conductive barrier layer, and the heat-sealable innermost layer, and is sealed in the easily-openable condition. The opening 2 is formed with a through hole provided on the laminated packaging material, and an area including an outer peripheral portion of the through hole is sealed with a pull-tag providing the barrier effect from the outer side and also with a patch film 5 from the inner side.

As shown in FIG. 3, a probe electrode 3 is provided on the patch film 5 from the inner side.

A plate-like earth electrode 4 having a length equivalent to a transversal width of the laminating packaging material is provided so that a conductive barrier layer on an end face 6 of the web-like laminated packaging material can be detected.

In this embodiment, the probe electrode and the earth electrode 4 are provided adjacent to each other in the outer side and in the inner side from the opening 3 respectively without mechanically contacting a surface of the laminated packaging material 1. Therefore, an outer surface of the laminated packaging material is not damaged by the electrodes (during inspection), and all products (packaging material and a packaging container) can be inspected on a production line.

Operations for detecting a defective sealed condition with the inspection apparatus according to the first embodiment are described with reference to FIG. 4.

The opening 2 is formed with a through hole provided on the laminated packaging material having a thermoplastic material outer most layer 7, a paper-made substrate layer 8, a conductive barrier layer 9, and a heat-sealable innermost layer 10, and an area including an outer peripheral portion of the through hole is sealed with the pull-tab 1 providing the barrier effect from the outer side and also with the patch film 5 from the inner side.

The conductive barrier layer is used for inspection, and conductivity of the barrier layer is utilized. A high voltage power line 12 is connected to a section between the probe electrode 3 and the earth electrode 4, and a high voltage is applied to the section. When any pin hole 14 is present on the patch film 5, inside of the barrier layer 9 is energized to flow a current between the probe electrode 3 and the earth electrode 4. A determining unit 13 detects conduction between the probe electrode 3 and the conductive barrier layer 9 provided on an end face of the through hole via the pin hole 14 on the patch film 5 to determine whether the sealed condition is defective or not.

When there is a pin hole in an insulated portion of the inner patch film, the probe electrode and the conductive barrier layer provided on an end face of the through hole are electrically connected to each other via the pin hole and furthermore inside of the conductive barrier layer is energized. Because the earth electrode is provided so that the conductive barrier layer on an end face of the web-like laminated packaging material can be detected, and therefore when there is any pin hole, an electric current flows between the probe electrode and the earth electrode via the conductive barrier layer.

As shown in the enlarged view in FIG. 4, the probe electrode 3 is pyriform and has a form covering up to an outer peripheral portion of the through hole. Therefore, even when a pin hole is present in the heat-sealable innermost layer at a position 15 off from the outer peripheral portion of the through hole, an electric current does not flow between the probe electrode 3 and the earth electrode 4, so that a malfunction of detecting a not-defective condition as a defective condition can be prevented.

In FIG. 5 showing an appearance of an inspection apparatus according to a second embodiment of the present invention and in FIG. 6 which is an enlarged view of FIG. 5, the opening 2 is formed with a through hole provided on the paper-made substrate layer 8, and an area including the through hole is sealed by laminating the thermoplastic material outermost layer 7, the conductive barrier layer 9, and the heat-sealable innermost layer 19.

Because of the configuration as described above, an opening can be inspected before the packaging material is formed into a container and a liquid content is filled in the container, namely, for instance, before the filling step with a packaging/filling machine shown in FIG. 3 is started.

Although the probe electrode 3 is shown in a simplified condition in FIG. 6, in the second embodiment of the present invention, the probe electrode has a form covering up to at least a peripheral portion of the through hole. A form the probe electrode 3 is shown in FIG. 7. In this example, the electrode 3 has a circular form covering a peripheral portion 72 of a through hole 71.

The probe electrode 3 is provided on the heat-sealable innermost layer 10 from the inner side.

Therefore, even when a pin hole is present in the heat-sealable innermost layer at a position 15 off from the outer peripheral portion of the through hole, an electric current does not flow between the probe electrode 3 and the earth electrode 4, so that a malfunction of detecting a not-defective condition as a defective condition can be prevented.

Furthermore, because the earth electrode has a form covering up to an outré peripheral portion of the through hole, a malfunction of providing conduction electric connection to the conductive barrier layer 9 provided on an end face of the web-like laminated packaging material never occurs.

In this embodiment, the determining unit 13 detects a conductive condition caused by a void 14 penetrating the thermoplastic material outermost layer 7, the conductive barrier layer 9, and the heat-sealable innermost layer inside the through hole to determine whether the sealed condition is defective or not.

In the sealed condition inspection according to a third preferable embodiment of the present invention, inspection is made for a formed container or a container with a content filled therein.

The embodiment is described with reference to FIG. 8, FIG. 9, and FIG. 9. In the sealed condition inspection according to the embodiment, the opening 2 at a vertex 21 of a container 80 with a content 81 filled therein is formed with a through hole on the paper-made substrate layer 8, and an area including the through hole is sealed by laminating the thermoplastic material outermost layer 7, the conductive barrier layer 9, and the heat-sealable innermost layer 10.

The probe electrode 3 having a form covering up to at least a peripheral portion of the through hole is provided on the thermoplastic material outermost layer 7 from the outer side.

The earth electrode 4 is provided so that the conductive barrier layer 9 provided on an end face 82 of the laminated packaging material having been formed into a container can be detected. In this example, the earth electrode 4 having a plate-like form is provided so that the earth electrode 4 contacts a bottom of the container. The high voltage power line 12 is connected to a section between the probe electrode 3 and the earth electrode 4 and a high voltage is applied to the section.

When any defect is detected during the sealed condition inspection according to the present invention, there is generated the void 14 penetrating the thermoplastic material outermost layer 7, the conductive barrier layer 9, and the heat-sealable innermost layer 10 inside the through hole. The conductive barrier layer 9 is exposed on an end face of the void or the pin hole, and the determining unit 13 detects the electric connection to determine that the sealed condition is defective.

In this embodiment, inspection is performed after a final product is manufactured. Because of the feature, a product with high reliability can be shipped.

When the web-like packaging material is formed into a container, the conductive barrier layer provided on an end face of various types of laminated packaging materials is exposed according to a bending way. Electric connection can be realized by making use of the exposed face.

Furthermore, the earth electrodes 4 having various forms can be used. FIG. 9 illustrates a variant. In this example, the opening 2 provided at a vertex of the container 80 is sealed by laminating the thermoplastic material outermost layer 7, the conductive barrier layer 9, and the heat-sealable innermost layer 10. The probe electrode 3 is provided from the outer side from the opening 2. The earth electrode 4 is provided so that the conductive barrier layer 9 provided on an end face of the laminated packaging material having been formed into a container can be detected. In this example, the earth electrode 4 made of a fibrous metal is provided so that the earth electrode 4 contacts a bottom of the container. The high voltage power line 12 is connected to a section between the probe electrode 3 and the earth electrode 4, and a high voltage is applied to the section.

FIG. 10 and FIG. 11 each illustrate a model in which the inspection apparatus according to the third embodiment of the present invention is incorporated in a production line. In this model, the containers 80 are successively transferred by a belt conveyor 101. A vertical conveyor 102 for transferring each container 80 gripping from the side face side is provided on the way of the line, and the probe electrode 3 is provided above the vertical conveyor 102 and the earth electrode 4 is provided under the vertical conveyor 102. If any defect is detected during the sealed condition inspection according to the embodiment, a the conductive barrier layer is exposed on an end face of the void or the pin hole, and an electric current flows between the probe electrode 3 and the earth electrode 4 via the conductive surface, and the determining unit detects the electrically connected condition to determine that the sealed condition is defective.

When it is determined that the sealed condition is defective, a defective product take-out device 103 activates a pusher 104 to remove the defective container from the production line.

The present invention is not limited to the embodiments described above, and various modifications are allowable within the gist of the present invention, and the modifications are included in a scope of the present invention.

INDUSTRIAL APPLICABILITY

The packaging container according to the present invention can be applied to a packaging container with a liquid food such as juice or milk filled therein.

The invention claimed is:

1. A sealed condition inspection apparatus that inspects an opening provided on a laminated packaging material having a thermoplastic outermost layer, a paper-made substrate layer, a conductive barrier layer, and a heat-sealable innermost layer, the opening prepared by partially cutting at least the thermoplastic outermost layer and the paper-made substrate layer and also the opening sealed in an easily-openable condition, the sealed condition inspection apparatus comprising a needle-shaped probe electrode and an earth electrode positionable on opposite sides of the opening, with the probe electrode configured so it only covers the opening; and a determining unit which detects current flowing between the probe electrode while out of mechanical contact with the laminated packaging material and the earth electrode via the conductive barrier layer to thus indicate that a defect exists in a sealed condition of the opening.

2. The sealed condition inspection apparatus according to claim 1, wherein
the opening is a through hole in the laminated packaging material and the through hole is sealed with a barrier pull-tag extending across the through hole and fixed to an outside of the laminated packaging material and with a patch film extending across the through hole and fixed to an inner side of the laminated packaging material;
the probe electrode is configured to cover the through hole up to an outer peripheral portion of the through hole and is positionable to face the patch film from the inner side of the laminated packaging material;
the earth electrode is configured to detect the conductive barrier layer on at least one end face of the laminated packaging material; and
the determining unit detects conduction between the probe electrode and the conductive barrier layer on the end face of the through hole via the patch film to determine whether the sealed condition is defective or not.

3. The sealed condition inspection apparatus according to claim 1, wherein
the opening is a through hole in the paper-made substrate layer and an area including the through hole is sealed by laminating the thermoplastic material outermost layer, the conductive barrier layer, and the heat-sealable innermost layer;
the probe electrode is configured to cover up to an outer peripheral portion of the through hole and is provided on the heat-sealable innermost layer from an inner side of the laminated packaging material;
the earth electrode is configured to cover up to an outer peripheral portion of through hole and is provided on the thermoplastic material outermost layer from an outer side of the laminated packaging material; and
the determining unit detects conduction by a void penetrating the thermoplastic material outermost layer, the conductive barrier layer, and the heat-sealable innermost layer inside the through hole to determine whether the sealed condition is defective or not.

4. The sealed condition inspection apparatus according to claim 1, wherein
the opening is provided at a vertex portion of a container and is a through hole in the paper-made substrate layer, and an area including the through hole is sealed by laminating the thermoplastic material outermost layer, the conductive barrier layer, and the heat-sealable innermost layer;
the probe electrode is configured to cover at least an outer peripheral portion of the through hole and is provided on the thermoplastic outermost layer from an outer side of the laminated packaging material;
the earth electrode is configured to detect the conductive barrier layer at least at one end face of the laminated packaging material formed on the container; and
the determining unit detects conduction via the conductive barrier by a void penetrating the thermoplastic material outermost layer, the conductive barrier layer, and the heat-sealable innermost layer inside the through hole to determine whether the sealed condition is defective or not.

5. A method of inspecting an opening provided on a laminated packaging material having a thermoplastic outermost layer, a paper-made substrate layer, a conductive barrier layer, and a heat-sealable innermost layer, the opening prepared by partially cutting at least the thermoplastic outermost layer and the paper-made substrate layer, and the opening being sealed in the easily-openable condition, the method comprising:
applying voltage between a needle-shaped probe electrode which is not in mechanical contact with the laminated packaging material and an earth electrode positioned on opposite sides of the opening, the probe electrode being positioned to only cover the opening;
detecting current flowing between the probe electrode and the earth electrode via the conductive barrier layer; and
determining that a sealed condition of the opening is defective when current is detected to be flowing between the probe electrode and the earth electrode.

6. The sealed condition inspection method according to claim 5, wherein the opening is a through hole in the laminated packaging material, and the through hole is sealed with a barrier pull-tag fixed to an outer peripheral portion of the laminated packaging material around the through hole from an outer side and with a patch film fixed to an outer peripheral portion of the laminated packaging material around the through hole from an inner side;
the method further comprising:
positioning the probe electrode to cover the through hole up to an outer peripheral portion of the through hole and so that the probe electrode faces the patch film from an inner side of the laminated packaging material;
positioning the earth electrode to permit detection of the conductive barrier layer on at least one end face of the laminated packaging material; and
detecting conduction between the probe electrode and the conductive barrier layer on the end face of the through hole via the patch film to determine whether the sealed condition is defective or not.

7. The sealed condition inspection method according to claim 5, wherein the opening is a through hole in the paper-made substrate layer and an area including the through hole is sealed by lamination the thermoplastic material outermost layer, the conductive barrier layer, and the heat-sealable innermost layer;
the method further comprising:
positioning the probe electrode to cover up to an outer peripheral portion of the through hole and to face the heat-sealable innermost layer from an inner side of the laminated packaging material;
positioning the earth electrode to cover the through hole up to an outer peripheral portion of the through hole and to face the thermoplastic material outermost layer from an outer side of the laminated packaging material; and
determining conduction of the current by a void penetrating the thermoplastic material outermost layer, the conductive barrier layer, and the heat-sealable innermost layer inside the through hole to determine whether the sealed condition is defective or not.

8. The sealed condition inspection method according to claim 5, wherein the opening is at a vertex portion of a container and is a through hole provided on the paper-made substrate layer, and an area including the through hole is sealed by lamination of the thermoplastic material outermost layer, the conductive barrier layer, and the heat-sealable innermost layer;

the method further comprising:

positioning the probe electrode to cover up to an outer peripheral portion of the through hole and to face the thermoplastic outermost layer from an outer side of the laminated packaging material;

positioning the earth electrode so that the conductive barrier layer, at least at one end face of the laminated packaging material formed on the container, can be detected; and determining conduction of the current via the conduction barrier by a void penetrating the thermoplastic material outermost layer, the conductive barrier layer, and the heat-sealable innermost layer inside the through hole to determine whether the sealed condition is defective or not.

* * * * *